(12) United States Patent
Kang et al.

(10) Patent No.: US 10,660,679 B2
(45) Date of Patent: May 26, 2020

(54) SURGICAL SCREW AND FUSION DEVICE USING THE SAME

(71) Applicant: L&K BIOMED CO., LTD., Yongin-si, Gyeonggi-do (KR)

(72) Inventors: Gook-Jin Kang, Seoul (KR); Sun Kak Choi, Gwangju-si (KR)

(73) Assignee: L&K BIOMED CO., LTD., Yongin-si, Gyeonggi-do (KR)

( * ) Notice: Subject to any disclaimer, the term of this patent is extended or adjusted under 35 U.S.C. 154(b) by 105 days.

(21) Appl. No.: 15/768,807

(22) PCT Filed: Jun. 23, 2016

(86) PCT No.: PCT/KR2016/006656
§ 371 (c)(1),
(2) Date: Apr. 16, 2018

(87) PCT Pub. No.: WO2017/069375
PCT Pub. Date: Apr. 27, 2017

(65) Prior Publication Data
US 2018/0296261 A1  Oct. 18, 2018

(30) Foreign Application Priority Data
Oct. 19, 2015  (KR) .................. 10-2015-0145418

(51) Int. Cl.
*A61B 17/80*  (2006.01)
*A61B 17/86*  (2006.01)
(Continued)

(52) U.S. Cl.
CPC .......... *A61B 17/8047* (2013.01); *A61B 17/70* (2013.01); *A61B 17/7058* (2013.01);
(Continued)

(58) Field of Classification Search
CPC combination set(s) only.
See application file for complete search history.

(56) References Cited

U.S. PATENT DOCUMENTS

| 6,398,783 B1 | 6/2002 | Michelson |
| 7,625,379 B2 | 12/2009 | Puno et al. |

(Continued)

FOREIGN PATENT DOCUMENTS

| KR | 10-2007-0084011 A | 8/2007 |
| KR | 10-1040515 B1 | 6/2011 |
| KR | 10-2011-0106863 A | 9/2011 |

OTHER PUBLICATIONS

English translation of International Search Report for PCT/KR2016/006656, dated Sep. 22, 2016.
(Continued)

*Primary Examiner* — Sameh R Boles
(74) *Attorney, Agent, or Firm* — Medler Ferro Woodhouse Mills PLLC

(57) ABSTRACT

The present invention relates to a surgical screw capable of self-locking and a fusion device using the same. The screw includes: a screw body having a body main thread formed on an outer circumferential surface thereof, a body locking thread spaced apart from the body main thread with an offset portion interposed therebetween, and a body driving groove formed in the upper portion thereof; and a sleeve having a sleeve thread formed on an inner circumferential surface thereof to be screwed with the body locking thread, and a sleeve stopper spaced downwards from the sleeve thread so as to support the body locking thread. The surgical screw may also be included in a fusion device in a different form by coupling with a plate or a cage.

12 Claims, 7 Drawing Sheets

(51) Int. Cl.
    *A61F 2/44*           (2006.01)
    *A61B 17/72*         (2006.01)
    *A61B 17/70*         (2006.01)
    *A61F 2/30*          (2006.01)

(52) U.S. Cl.
    CPC .............. *A61B 17/72* (2013.01); *A61B 17/86* (2013.01); *A61B 17/8605* (2013.01); *A61F 2/30749* (2013.01); *A61F 2/44* (2013.01); *A61F 2/447* (2013.01); *A61F 2002/30622* (2013.01)

(56) References Cited

U.S. PATENT DOCUMENTS

| | | |
|---|---|---|
| 7,846,207 B2 | 12/2010 | Lechmann et al. |
| 8,075,604 B2 | 12/2011 | Denis et al. |
| 8,328,872 B2 | 12/2012 | Duffield et al. |
| 8,449,585 B2 | 5/2013 | Wallenstein et al. |
| 8,795,373 B2 | 8/2014 | Jones et al. |
| 2012/0271423 A1* | 10/2012 | Wallenstein ............ A61F 2/447 623/17.16 |

OTHER PUBLICATIONS

English translation of International Search Report for PCT/KR2016/066654, dated Sep. 22, 2016.

\* cited by examiner

[FIG. 1]
200
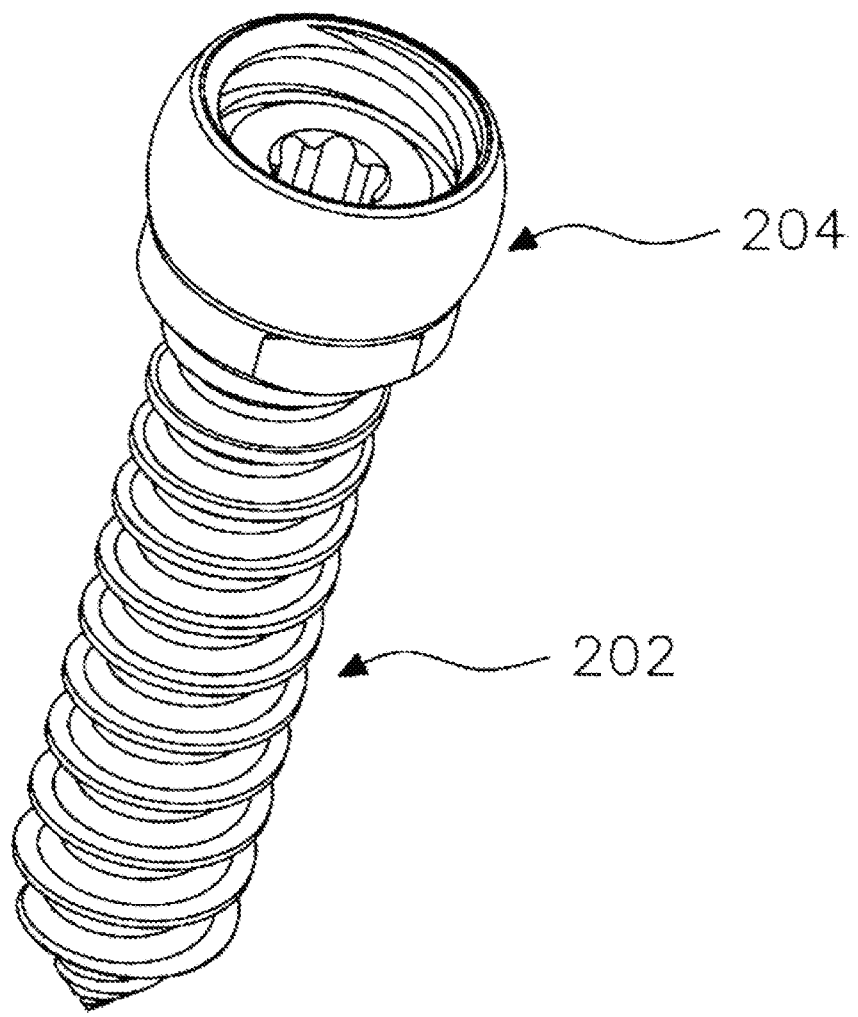

[FIG. 2]
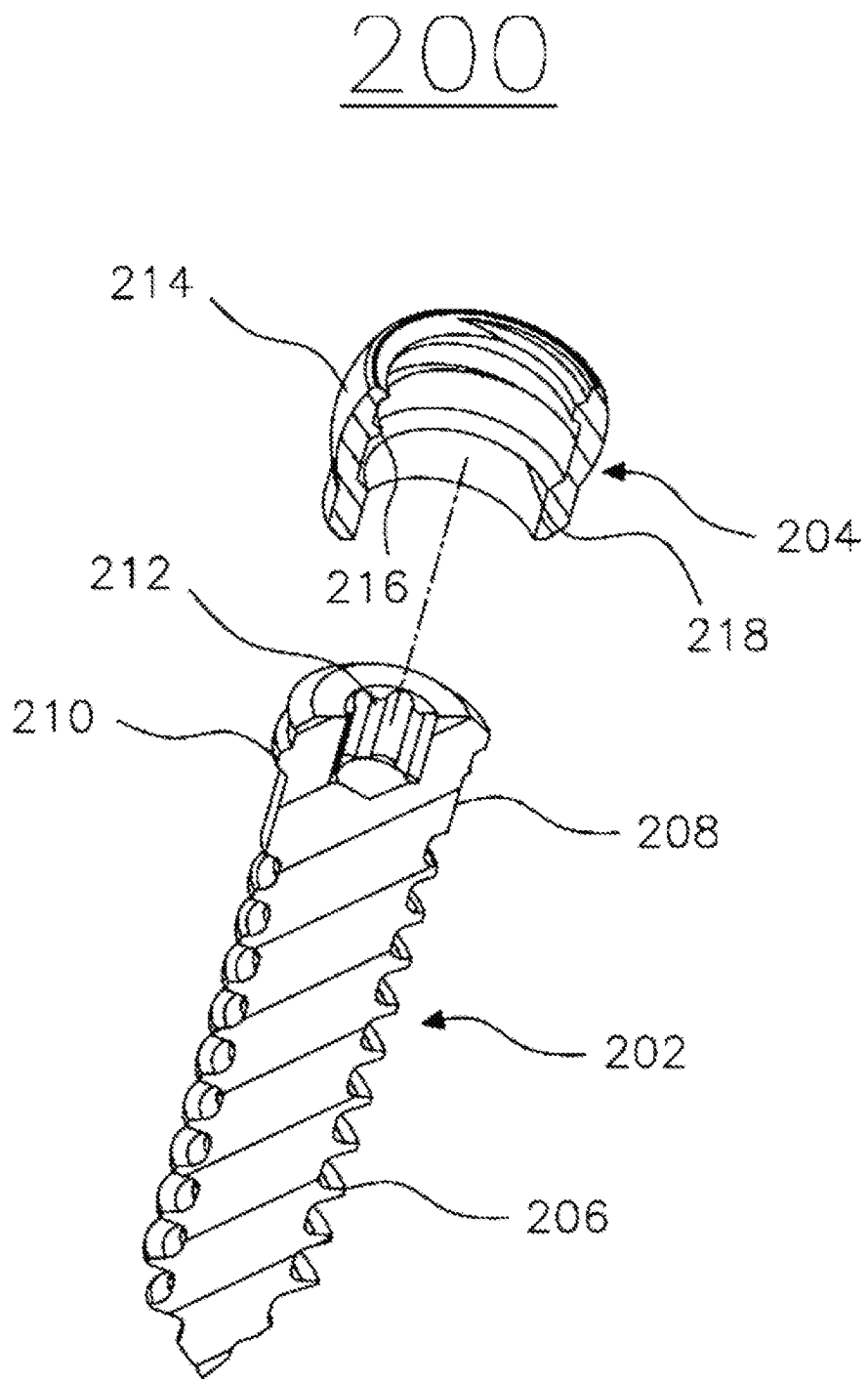

[FIG. 3]
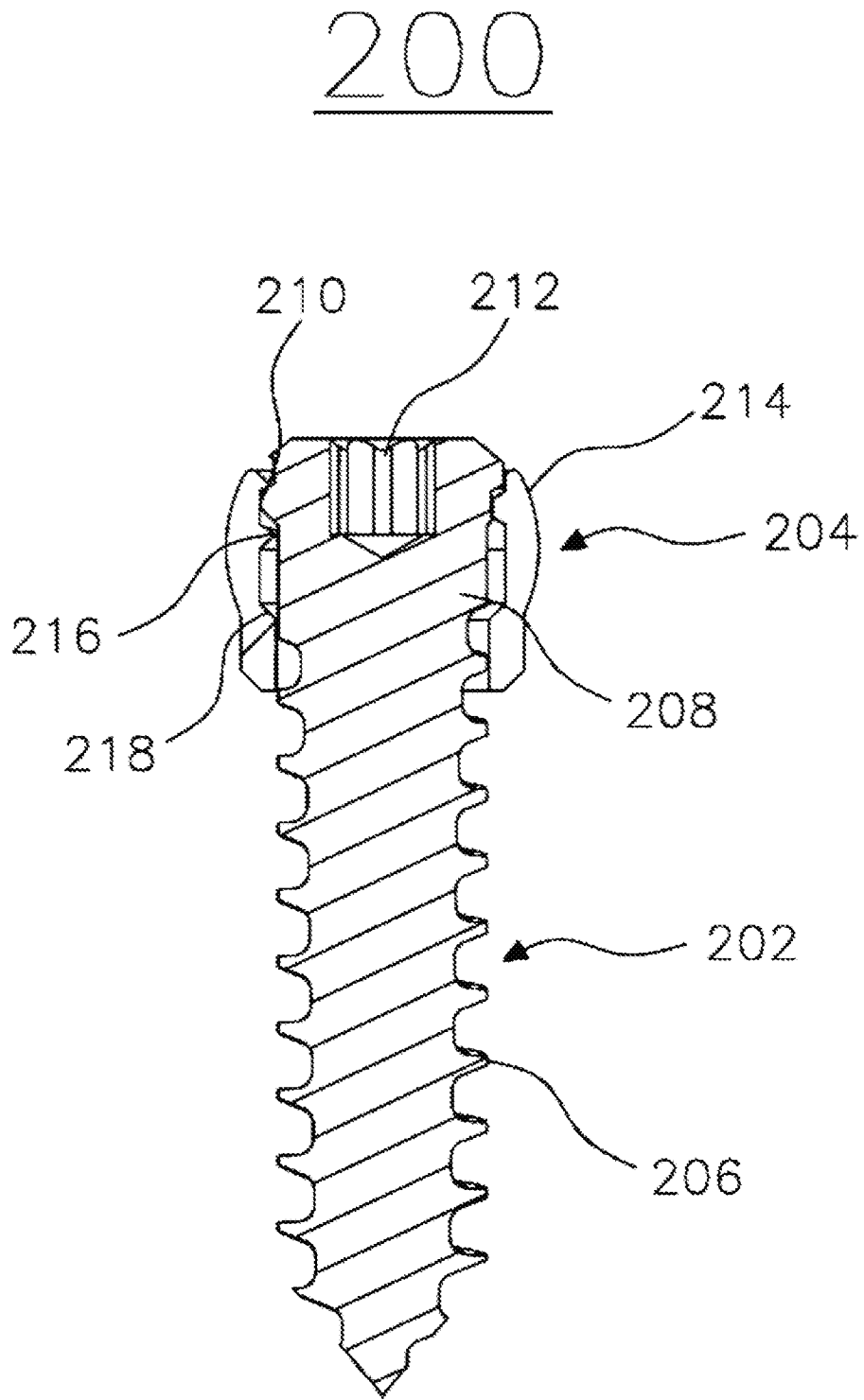

[FIG. 4]
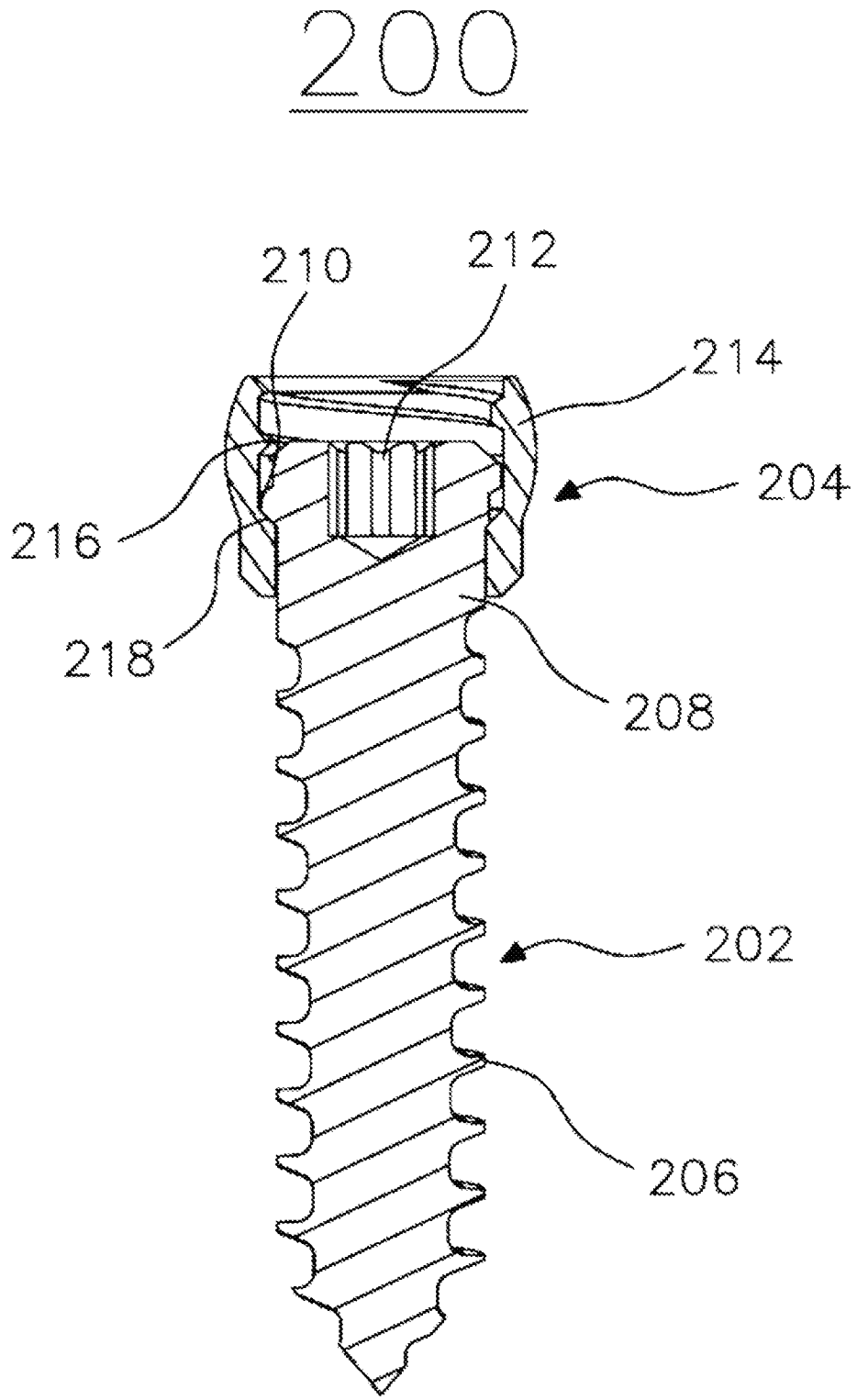

[FIG. 5]
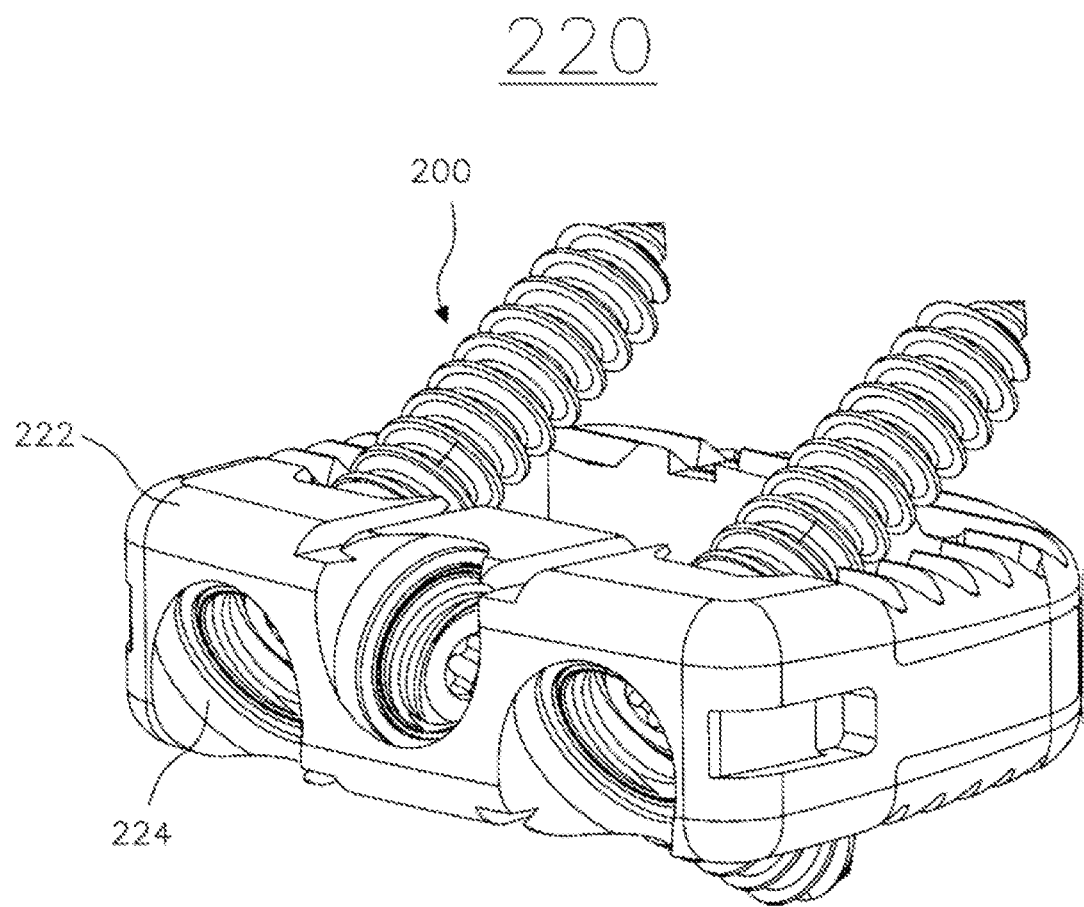

[FIG. 6]
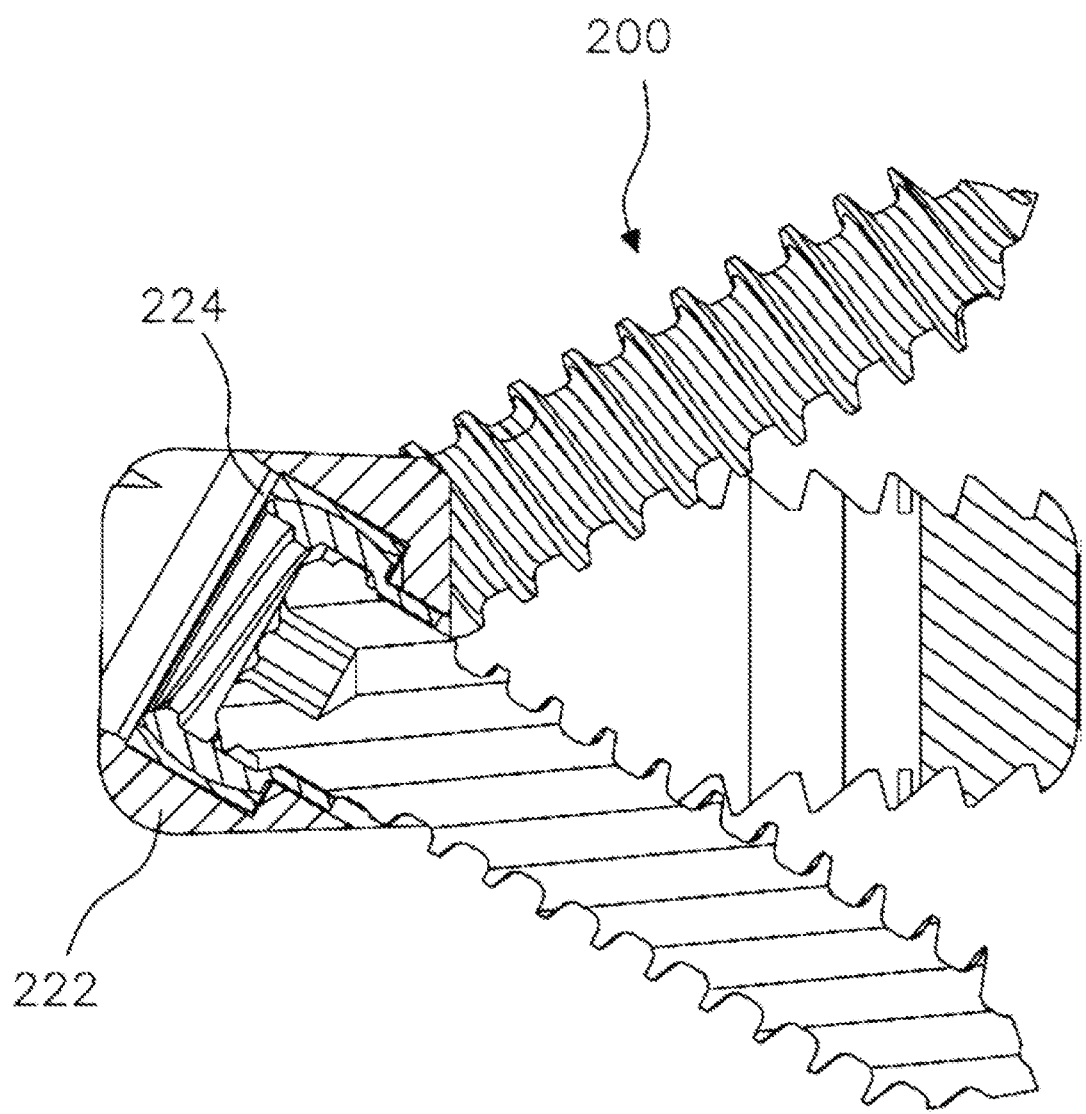

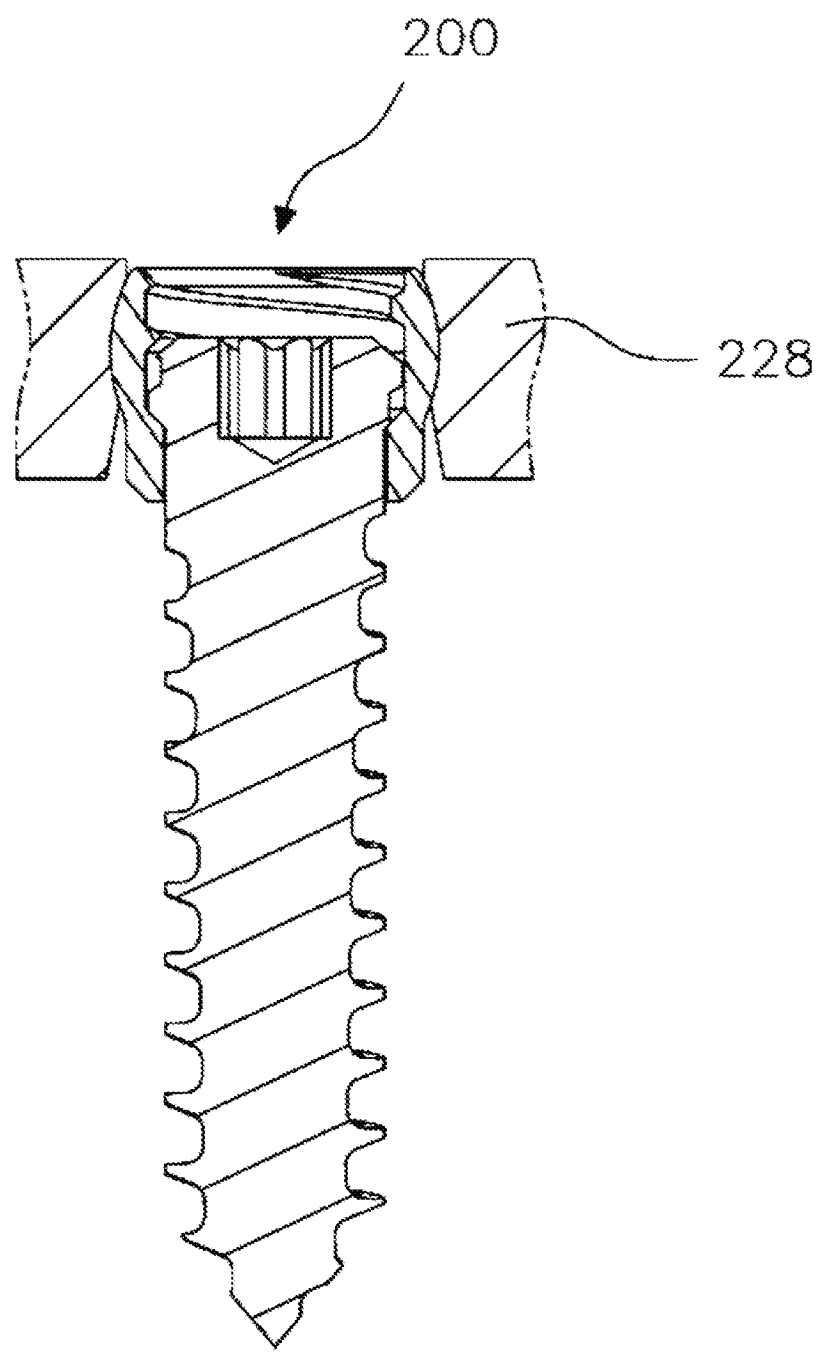

SURGICAL SCREW AND FUSION DEVICE USING THE SAME

TECHNICAL FIELD

The present invention relates to a surgical screw and a fusion device using the same, and more particularly, to a surgical screw capable of self-locking and a fusion device using the same.

BACKGROUND ART

Various types of fasteners are used to fasten implants and other devices to bones. In a spinal field, bone screws are typically used in order to attach plates, rods, and the like of implants and devices to one or more vertebral bodies.

Various techniques have been developed to fix the bone screws to the vertebral bodies, or prevent the bone screws from being separated from the plates or rods of the implants and devices. For example, U.S. Pat. No. 7,846,207 discloses a technique in which a cage may be inserted between vertebral bodies and bone screws may be attached to the vertebral bodies to fix the cage. The above patent proposes a method in which, a securing plate is further provided on a head side of the bone screw to prevent the bone screw from being pulled out, and the securing screw is coupled to the cage by passing it through the securing plate.

In addition, U.S. Pat. No. 6,398,783 discloses a locking element that rotates around a hole into which the bone screw is inserted, which is installed in a plate to prevent the bone screw from being pulled out when fixing the plate to the vertebral body.

Further, U.S. Pat. No. 7,625,379 discloses using two nuts in an SI joint fusion implant to prevent the bone screw from being pulled out, which is used when a problem occurs in a joint between a sacrum and an ilium (pelvis).

As such, various techniques for preventing the bone screw from being pulled out in various areas are considered and disclosed in the art, but there is a disadvantage that a separate locking mechanism should be used for this purpose. Therefore, there is a need to develop a screw which can easily maintain the locked state without the separate locking mechanism.

PRIOR ART DOCUMENT

Patent Document (Patent Document 1) U.S. Pat. No. 7,846,207
(Patent Document 2) U.S. Pat. No. 6,398,783
(Patent Document 3) U.S. Pat. No. 7,625,379

SUMMARY OF INVENTION

Problems to be Solved by Invention

In consideration of the above-mentioned circumstances, it is an object of the present invention to provide a surgical screw capable of self-locking without a separate locking mechanism and a fusion device using the same.

Means for Solving Problems

In order to achieve the above object, according to an aspect of the present invention, there is provided a surgical screw including: a screw body having a body main thread formed on an outer circumferential surface thereof, a body locking thread formed on the outer circumferential surface thereof apart from the body main thread with an offset portion interposed therebetween, and a body driving groove formed in an upper portion thereof; and a sleeve having a sleeve thread formed on an inner circumferential surface thereof to be screwed with the body locking thread, and a sleeve stopper spaced apart downwards from the sleeve thread to support the body locking thread.

The sleeve stopper may have an inner circumferential surface on a lower portion thereof coinciding with an outer circumferential surface of the offset portion.

The body locking thread may have the same pitch and outer diameter as the body main thread, and the offset portion may have a length of an integral multiple of a pitch of the body main thread.

The body locking thread or the sleeve thread may have a lead height one time or less of a pitch of the body locking thread.

In addition, according to another aspect of the present invention, there is provided a fusion device including: the surgical screw according to the present invention; and a plate in which the surgical screw is installed.

Further, according to another aspect of the present invention, there is provided a fusion device including: the surgical screw according to the present invention; and a cage having a through hole in which the surgical screw penetrates.

Advantageous Effects

According to the present invention, it is possible to provide a surgical screw which can easily maintain a locked state without a separate locking mechanism and a fusion device including the same. In addition, since the surgical screw has no separate locking mechanism, there is an advantage that the number of tools for locking the screw is reduced, and the operator's labor and procedure time are reduced.

BRIEF DESCRIPTION OF DRAWINGS

FIG. 1 is a perspective view illustrating a surgical screw according to an embodiment of the present invention.

FIG. 2 is an exploded perspective view of the surgical screw of FIG. 1.

FIG. 3 is a cross-sectional view illustrating a state in which the surgical screw of FIG. 1 is pulled out.

FIG. 4 is a cross-sectional view illustrating a state in which the surgical screw of FIG. 1 is locked.

FIG. 5 is a perspective view illustrating an example of a fusion device using the surgical screw according to the embodiment of the present invention.

FIG. 6 is a cross-sectional view of the fusion device of FIG. 5.

FIG. 7 is a cross-sectional view illustrating another example of the fusion device using the surgical screw according to the embodiment of the present invention.

MODE FOR CARRYING OUT INVENTION

The present invention has an object to provide a surgical screw capable of self-locking without a separate locking mechanism and a fusion device using the same.

Hereinafter, the present invention will be described in detail with reference to the accompanying drawings. In denoting reference numerals to constitutional elements of respective drawings, it should be noted that the same elements will be denoted by the same reference numerals although they are illustrated in different drawings. In the embodiments of the present invention, the publicly known functions and configurations that are judged to be able to make the purport of the present invention unnecessarily obscure will not be described.

FIGS. 1 to 4 illustrate a surgical screw 200 according to an embodiment of the present invention. The surgical screw 200 basically includes a screw body 202 and a sleeve 204 fastened to the screw body 202.

The screw body 202 has a body main thread 206 formed on an outer circumferential surface thereof and a body locking thread 210 formed on the outer circumferential surface thereof apart from the body main thread 206 with an offset portion 208 interposed therebetween. The body locking thread 210 may have the same or a larger outer diameter as or than the body main thread 206. In this regard, when the screw body 202 rotates, in order to allow the body locking thread 210 and the body main thread 206 to be screwed with a thread formed in the bone at the same time, it is preferable that the body locking thread 210 has the same outer diameter as the body main thread 206.

For the same reason, it is preferable that the offset portion 208 has a length of an integral multiple of a pitch of the body main thread.

The screw body 202 has a body driving groove 212 formed in an upper portion thereof to receive a rotational force from a tool such as a screwdriver.

The sleeve 204 has a sleeve thread 216 formed on an inner circumferential surface thereof to be screwed with the body locking thread 210, and a sleeve stopper 218 spaced apart downwards from the sleeve thread 216 so as to support the body locking thread 210.

That is, the sleeve thread 216 is screwed with the body locking thread 210 only by a small amount of rotation, and then, by moving the body locking thread 210 to a lower side of the sleeve thread 216, a lower surface of the sleeve thread 216 serves as a stopper to prevent the body locking thread 210 from being pulled out. Further, the sleeve stopper 218 serves to prevent the body locking thread 210, which has been moved to the lower side of the sleeve thread 216, from further moving downward.

In addition, by making a coupling section of the sleeve thread 216 with the body locking thread 210 not to be too long, the entire height of the sleeve 204 may be decreased, and a burden of labor required by an operator may be reduced due to a frictional force generated when the sleeve thread 216 and the body locking thread 210 are screwed with each other. To this end, it is preferable that the body locking thread 210 or the sleeve thread 216 has a lead height one time or less of a pitch of the body locking thread 210.

Thus, the sleeve stopper 218 has an inner circumferential surface on a lower portion thereof coinciding with an outer circumferential surface of the offset portion 208, so that the offset portion 208 is guided by the lower portion of the sleeve stopper 218. As a result, it is possible to secure straightness of the screw body 202 with respect to the sleeve 204.

The sleeve 204 has a sleeve body 214 which may be formed in various shapes as necessary and may be rotated in a plate, a cage, or the like when an outer circumference thereof is formed in a spherical surface.

FIGS. 5 and 6 illustrate a fusion device 220 using the surgical screw 100 according to the embodiment of the present invention. The fusion device 220 includes a cage 222 inserted between vertebral bodies and the surgical screws 200 inserted into through holes 224 formed in the cage 222. Since the surgical screw 200 is equipped with the sleeve 126 having the sleeve body 214 whose outer surface is formed in a curved surface, the surgical screw 200 can rotate within the through hole 224 in a predetermined range. Since the surgical screws 200 are screwed with the vertebral bodies while the surgical screws 200 are self-locked to the cage 222, there is an advantage that an additional locking device is not required.

FIG. 7 illustrates another fusion device 226 using the surgical screw 200 according to the embodiment of the present invention. The fusion device 226 includes a plate 228 which is in contact with a bone such as a vertebral body, and a surgical screw 200 which is installed in the plate 228. Therefore, since the surgical screw 200 is seated on the plate 228 and self-locked, there is an advantage that an additional locking device is not required. Further, since the surgical screw 200 is equipped with the sleeve 126 having the sleeve body 214 whose outer surface is formed in a curved surface, the surgical screw 200 can rotate within the through hole 224 in a predetermined range.

While the present invention has been described with reference to the preferred embodiments and modified examples, the present invention is not limited to the above-described specific embodiments and the modified examples, and it will be understood by those skilled in the related art that various modifications and variations may be made therein without departing from the scope of the present invention as defined by the appended claims.

DESCRIPTION OF REFERENCE NUMERALS

200: Surgical screw
202: Screw body
204: Sleeve
206: Body main thread
208: Offset portion
210: Body locking thread
212: Body driving groove
214: Sleeve body
216: Sleeve thread
218: Sleeve stopper
220, 226: Fusion device
222: Cage
224: Through hole
228: Plate

INDUSTRIAL APPLICABILITY

According to the present invention, it is possible to provide a surgical screw which can easily maintain a locked state without a separate locking mechanism and a fusion device including the same. In addition, since the surgical screw has no separate locking mechanism, there is an advantage that the number of tools for locking the screw is reduced, and the operator's labor and procedure time are reduced.

The invention claimed is:

1. A surgical screw comprising:
a screw body having a body main thread formed on an outer circumferential surface thereof, a body locking thread formed on the outer circumferential surface thereof apart from the body main thread with an offset portion interposed therebetween, and a body driving groove formed in an upper portion thereof; and
a sleeve having a sleeve thread formed on an inner circumferential surface thereof to be screwed with the body locking thread, and a sleeve stopper spaced apart downwards from the sleeve thread to support the body locking thread, so as to prevent the body locking thread, which has been moved to a lower side of the sleeve thread, from further moving downward, wherein, when moving the body locking thread screwed with the sleeve in the axial direction of the distal end of the screw body, a lower surface of the sleeve thread serves to prevent the body locking thread from being pulled out.

2. The surgical screw according to claim 1, wherein the sleeve stopper has an inner circumferential surface on a lower portion thereof coinciding with an outer circumferential surface of the offset portion.

3. A fusion device comprising:
the surgical screw according to claim 2; and
a plate in which the surgical screw is installed.

4. A fusion device comprising:
the surgical screw according to claim 2; and
a cage having a through hole in which the surgical screw penetrates.

5. The surgical screw according to claim 1, wherein the body locking thread has the same pitch and outer diameter as the body main thread, and the offset portion has a length of an integral multiple of a pitch of the body main thread.

6. A fusion device comprising:
the surgical screw according to claim 5; and
a plate in which the surgical screw is installed.

7. A fusion device comprising:
the surgical screw according to claim 5; and
a cage having a through hole in which the surgical screw penetrates.

8. The surgical screw according to claim 1, wherein the body locking thread or the sleeve thread has a lead height one time or less of a pitch of the body locking thread.

9. A fusion device comprising:
the surgical screw according to claim 8; and
a plate in which the surgical screw is installed.

10. A fusion device comprising:
the surgical screw according to claim 8; and
a cage having a through hole in which the surgical screw penetrates.

11. A fusion device comprising:
the surgical screw according to claim 1; and
a plate in which the surgical screw is installed.

12. A fusion device comprising:
the surgical screw according to claim 1; and
a cage having a through hole in which the surgical screw penetrates.

\* \* \* \* \*